United States Patent [19]

Miller

[11] Patent Number: 5,157,193

[45] Date of Patent: Oct. 20, 1992

[54] PREPARING LOWER ALKENES FROM METHANOL

[75] Inventor: Jorge P. Miller, Bogota, Colombia

[73] Assignee: Energia Andina Ltd., New York, N.Y.

[21] Appl. No.: 641,505

[22] Filed: Jan. 15, 1991

[51] Int. Cl.$^5$ .................................. C07C 1/00
[52] U.S. Cl. .................................. 585/640
[58] Field of Search .......................... 585/640

[56] References Cited

FOREIGN PATENT DOCUMENTS 0109725 7/1982 Japan ..................... 585/640

Primary Examiner—Patrick P. Garvin
Assistant Examiner—E. D. Irzinski
Attorney, Agent, or Firm—Fleit, Jacobson, Cohn, Price, Holman & Stern

[57] ABSTRACT

Controlled ratios of ethylene to propylene are obtained in almost quantitative yields from catalytic dehydration of methanol when selected molecular sieve zeolites are used as catalysts and the methanol starting material is diluted with varying amounts of steam or inert gas.

24 Claims, 1 Drawing Sheet

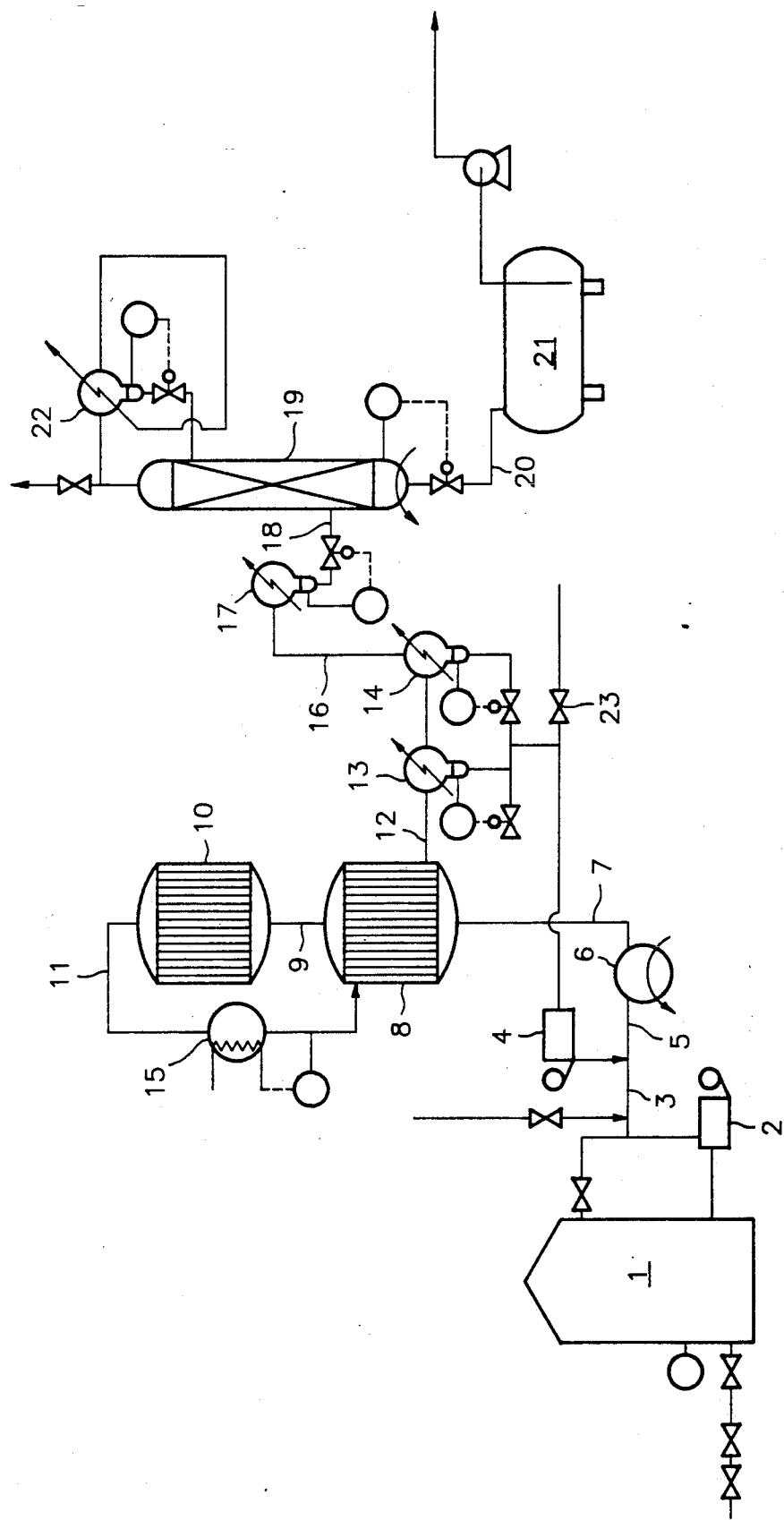

PREPARING LOWER ALKENES FROM METHANOL

FIELD OF THE INVENTION

Modified zeolite is used as catalyst in methanol dehydration to produce low molecular weight alkenes.

BACKGROUND

Methanol has been converted to olefins and aromatics by catalytic dehydration of methanol, using ZSM-5 acidic zeolite. The obtained product has a reported distribution as follows:

| | |
|---|---|
| Light Gas ($C_1$, $C_2$) | 1.3 |
| LPG ($C_3$, $C_4$) | 17.8 |
| Gasoline ($C_5$-$C_{12}$) | 80.9 |
| Aromatics (% of gasoline) | 38.6 |

SUMMARY OF THE INVENTION

A high yield of ethylene and propylene are obtained by catalytically dehydrating methanol in admixture with steam or an inert gas (which does not interfere with the reaction, e.g. nitrogen and methane) without forming higher alkenes or aromatics. The catalyst is a type-A, type-X or a type-Y molecular sieve zeolite in the aluminum and hydrogen form.

An object of this invention is to produce ethylene and propylene in high yield from methanol. A further object is to provide a non-polluting process for such production. A still further object is to devise a process wherein the proportion of ethylene to propylene produced is readily controlled. Another object is to produce ethylene and propylene economically.

BRIEF DESCRIPTION OF THE DRAWING

The sole figure of drawing is a schematic flow diagram of the disclosed process.

DETAILS

Catalytic dehydration of methanol to form ethylene and propylene proceeds according to the following reaction schemes:

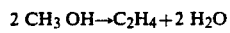

$$2\ CH_3OH \rightarrow C_2H_4 + 2\ H_2O$$

$$3\ CH_3OH \rightarrow C_3H_6 + 3\ H_2O$$

Both of these reactions are exothermic.

The reactions are conducted continuously in a column reactor and in vapor phase, generally at temperatures from about 250° to about 320° C. and at a pressure ranging from atmospheric pressure to 20 bar.

With reference to the drawings, methanol from storage tank 1 is pumped through pump 2 to line 3 at a pressure of from atmospheric pressure to 10 bar. Water is pumped through pump 4 at a pressure of up to 10 bar. (Alternatively, inert gas, such as nitrogen or methane, is fed directly into the feed superheater 8.)

Line 5 receives methanol and diluting water, and delivers the resulting solution to feed vaporizer 6. Vaporized feed is transmitted through line 7 to feed superheater 8, in which the temperature is raised to 180° C. Superheated vapors from the feed superheater are passed through line 9 to tubular reactor 10, which is filled with catalyst inside tubes. Converted methanol exhausting from the reactor at 300° C. is passed through line 11. Gases containing converted methanol subsequently serve to preheat feed in the feed superheater and subsequently exhaust through line 12. They are then cooled and condensed by condensers 13 and 14.

Optionally, converted methanol exhausting through line 11 is passed though an auxillary heater 15 prior to being used for preheating in the feed superheater 8.

Condenser 14 eliminates practically all of the water and slight amounts of unconverted methanol. Dry gases from condenser 14 are conducted through line 16 to condenser 17, in which they are cooled to −40° C. prior to introduction through line 18 to splitter 19. Ethylene and propylene are conventionally separated in the splitter, from which propylene is conveyed through line 20 to storage tank 21, and ethylene evaporation heat is used to condense reflux through condenser 22.

Water from condensers 13 and 14 is returned to pump 4 for recycling to the system. Excess water is discharged through valve 23.

The ratio between ethylene and propylene produced is determined by the volume ratio between pump 4 and pump 2. Residence time for methanol in reactor 10 is determined in accord with well-established chemical engineering principles, as are methods for recovering produced ethylene and propylene.

PRODUCT CONTROL

The ratio of ethylene to propylene in the reaction product is readily varied widely from 5% ethylene and 95% propylene to 95% ethylene and 5% propylene by diluting the methanol feed with steam or an inert gas prior to passing the methanol through the catalyst. The higher the methanol dilution, the higher the proportion of ethylene to propylene obtained. The effect of dilution is shown in the following table.

| Feed | | Product | |
|---|---|---|---|
| Inert | Methanol | Ethylene | Propylene |
| 95 | 5 | 79.98 | 20.02 |
| 85 | 15 | 20.44 | 79.56 |
| 80 | 20 | 7.93 | 92.07 |

Passage of pure methanol through the catalyst at the involved temperatures leads to oligomerization of ethylene and propylene, producing higher molecular weight alkenes. The molar ratio of methanol to steam or inert gas is advantageously from 2 to 50 percent.

CATALYST

The catalyst is prepared by ion exchange of the sodium ions of a molecular sieve zeolite for aluminum and ammonium ions and subsequently driving off the ammonia, leaving the structure in the aluminum and hydrogen form. The zeolite is a type-A, a type-X or a type-Y molecular sieve zeolite which advantageously has an ammonium ion exchange capacity of from 4 to 7 equivalents per kilo.

Although practically all types (A, X, Y) are useful, type-A molecular sieve zeolites are preferred. Particularly those having a molar composition in the range of:

| | |
|---|---|
| $Al_2O_3$ | 1 ± 10% |
| $Na_2O$ | 1 ± 10% |
| $SiO_2$ | 2 ± 10% |

The optimum pore size of the zeolite is between 3 and 5 angstroms.

The composition or ratio between the aluminum sulfate and ammonium sulfate solution used to exchange sodium in the zeolite is optionally varied widely between a ratio of one equivalent of aluminum to 20 of ammonium and a ratio of 20 equivalents of aluminum to 1 of ammonium. The optimum is the proportion equivalent to ammonium alum. The concentration of the solution used to exchange the sodium optionally varies from 1% to saturated. Other soluble salts of ammonia and aluminum are optionally used in the exchange.

EXAMPLE 1 kilo of Baylith TE-144 (manufactured by Bayer in Germany) or its equivalent molecular sieve zeolite is placed in a column having a height to diameter ratio of 4 to 1. Water is passed downflow through the column in an amount sufficient to wet the zeolite spheres thoroughly.

A solution of ammonium alum [$NH_4 Al (SO_4)_2 \cdot 12 H_2O$], 5% by weight, is passed downwardly through the column at a low rate (1 cm. per second) until the outlet composition confirms that all sodium has been replaced. Completion of the exchange is normally assured by passing an excess amount of alum through the column.

The column filled with zeolite is then washed with pure water until the pH of the outlet is about 7. Once washed, the zeolite spheres are heated to about 300° C. until no more ammonia is detected. The catalyst is now ready.

To assure good heat transfer, the diameter of the reactor tubes should not exceed two inches. At a space velocity of 80 cm. per minute, with a bed height of 22 cm., and a temperature of 300° C., 94% conversion is obtained.

The invention and its advantages are readily understood from the preceding description. Various changes may be made in the compositions and in the process without departing from the spirit and scope of the invention or sacrificing its material advantages. The process and compositions hereinbefore described are merely illustrative of preferred embodiments of the invention.

What is claimed is:

1. A combination of a) methanol, b) steam or inert gas and c) molecular sieve zeolite in the aluminum and hydrogen form, wherein:
   the proportion of methanol to steam or inert gas in the combination of (a) and (b) ranges from 2 to 50 molar percent; and
   the zeolite is an A-type, an X-type or a Y-type zeolite.

2. A combination of claim 1 wherein the zeolite has an ammonium ion exchange capacity of from 4 to 7 equivalents per kilo.

3. A combination of claim 2 wherein the zeolite has a pore size of from 3 to 5 angstroms.

4. A combination of claim 3 wherein the zeolite is an A-type zeolite having a molar composition in the range of:

| | |
|---|---|
| $Al_2O_3$ | 1 ± 10% |
| $Na_2O$ | 1 ± 10% |
| $SiO_2$ | 2 ± 10% |

5. In a process for catalytic dehydration of methanol with a zeolite catalyst, the improvement wherein the catalyst is an A-type, X-type or Y-type molecular sieve zeolite in the aluminum and hydrogen form, the methanol is diluted with steam or an inert gas prior to dehydration, and the methanol is converted selectively to ethylene and propylene.

6. A process of claim 5 which comprises increasing the molar proportion of steam or inert gas is to increase the molar proportion of ethylene produced.

7. A process of claim 5 which comprises decreasing the molar proportion of steam or inert gas to increase the molar proportion of propylene produced.

8. A process of claim 5 which comprises diluting the methanol is with steam.

9. A process of claim 5 wherein said catalyst is an A-type molecular sieve zeolite.

10. A process of claim 5 which comprises:
    a) preparing a mixture of methanol with an amount of steam or inert gas,
    b) contacting the mixture, in vapor phase, with A-type, X-type or Y-type molecular sieve zeolite catalyst in the aluminum and hydrogen form and at a temperature sufficient to convert the methanol to a mixture of ethylene and propylene, and
    c) separating ethylene and propylene from the thus-obtained mixture.

11. A process of claim 10 wherein the amount of steam or inert gas in the mixture thereof with methanol is from 2 to 50 molar percent.

12. A process of claim 11 which comprises preheating the methanol mixture.

13. A process of claim 12 wherein the preheating is effected with heat from the mixture of ethylene and propylene produced by step (b).

14. A process of claim 11 wherein the mixture prepared in step (a) is a mixture of methanol with steam, and the catalyst is A-type molecular sieve zeolite having an ammonium ion exchange capacity of from 4 to 7 equivalents per kilo.

15. A process of claim 14 wherein the zeolite has a pore size of from 3 to 5 angstroms.

16. A process of claim 14 wherein the catalyst is in a column having a height to diameter ratio of about 4 to 1.

17. A process of claim 14 wherein step (b) comprises passing the mixture through a bed of the catalyst at a space velocity of about 80 cm. per minute and the catalyst bed has a height of about 22 cm.

18. A process of claim 14 wherein the mole ratio of methanol to steam in the mixture thereof is about 5 to 95.

19. A process of claim 14 wherein the mole rate of methanol to steam in the mixture thereof is about 15 to 85.

20. A process of claim 14 wherein the mole ratio of methanol to steam in the mixture thereof is about 20 to 80.

21. A combination of claim 1 wherein the zeolite is an A-type zeolite.

22. A combination of claim 1 wherein the zeolite is an X-type zeolite.

23. A combination of claim 1 wherein the zeolite is a Y-type zeolite.

24. In a process for catalytic dehydration of methanol, the improvement which comprises combining a) methanol, b) steam or inert gas and c) molecular sieve zeolite in the aluminum and hydrogen form, wherein:
    the proportion of methanol to steam or inert gas in the combination of (a) and (b) ranges from 2 to 50 molar percent; and
    the zeolite is an A-type, an X-type or a Y-type zeolite.

* * * * *